United States Patent [19]
Conley et al.

[11] Patent Number: 5,763,574
[45] Date of Patent: Jun. 9, 1998

[54] HIV-SPECIFIC SYNTHETIC ANTIGENS AND THEIR USE

[75] Inventors: Anthony J. Conley, Exton; Beth A. Arnold, Quakertown; Lynn J. Boots; Paul M. Keller, both of Lansdale, all of Pa.

[73] Assignee: Merck & Co., Inc., Rahway, N.J.

[21] Appl. No.: 625,691

[22] Filed: Apr. 4, 1996

Related U.S. Application Data

[63] Continuation of Ser. No. 323,338, Oct. 14, 1994, abandoned.
[51] Int. Cl.$^6$ .................... A61K 38/00; A61K 39/21; C07K 5/00; C07K 7/00
[52] U.S. Cl. .................... 530/326; 530/350; 530/395; 424/188.1; 424/184.1; 424/208.1; 424/204.1
[58] Field of Search ............... 424/188.1, 184.1, 424/204.1; 530/350, 395

[56] References Cited

FOREIGN PATENT DOCUMENTS

| | | | |
|---|---|---|---|
| 0467700 | 1/1992 | European Pat. Off. | C07K 7/06 |
| 0467714 | 1/1992 | European Pat. Off. | C07K 13/00 |
| 0471407 | 2/1992 | European Pat. Off. | C07K 17/02 |

OTHER PUBLICATIONS

Greene, 1993, "AIDS and the Immune System . . ." Scientific American, Sep. 1993, pp. 99–105.
Scott, et al, 1990, "Human monoclonal antibody that recognizes . . . ", PNAS 87:8597–8601.
Cwirla, et al, 1990, "Reptides on phage: a vast . . ." PNAS 87:6378–6382.
Schild, et al, 1990, "Human immunodeficiency Virus . . .". The Lancet vol. 335: 1081–1084.
Cohen, 1993, "Jitters Jeopardize AIDS . . ." Science vol. 262: 980–981.
Fox, "No Winners Against AIDS", Biotechnology vol. 12, p. 128, 1994.
Haynes, "Scientific and Social Issues of Human Immuno. . . ." Science, vol. 260, pp. 1279–1286, 1993.

*Primary Examiner*—Lynette F. Smith
*Attorney, Agent, or Firm*—Joseph A. Coppola; Joanne M. Giesser

[57] ABSTRACT

Immunological conjugates of HIV-specific selected principal neutralization epitopes are prepared. These epitopes bind 19b, a broadly neutralizing human monoclonal antibody specific for the HIV gp120. The epitopes are identified from oligopeptide epitope libraries. The conjugates are useful for vaccination against AIDS or ARC, as well as in the production of other HIV-specific broadly neutralizing antibodies for passive immunity against AIDS or ARC.

5 Claims, No Drawings

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Glu  Val  Asp  Met  Asp  Gly  Asn  Arg  Thr  Phe  Phe  Tyr  Val  Gly  Arg
 1                   5                        10                       15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Ser  Thr  Glu  Ile  Leu  Trp  Met  Gly  Ser  Gly  Arg  Gln  Phe  Tyr  Met
 1                   5                        10                       15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

```
Ser  Val  Ile  Met  Leu  Ala  Pro  Asp  Arg  Gly  Phe  Trp  Arg  Gly  Glu
 1                   5                        10                       15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:4:

```
Val  Met  Val  Val  Gly  Met  Asp  Pro  Gly  Arg  Ser  Phe  Phe  Gly  His
1                  5                        10                       15
```

(2) INFORMATION FOR SEQ ID NO:5:

(i) SEQUENCE CHARACTERISTICS:
        (A) LENGTH: 13 amino acids
        (B) TYPE: amino acid
        (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:5:

```
Xaa  Xaa  Xaa  Xaa  Met  Xaa  Pro  Xaa  Arg  Xaa  Phe  Xaa  Xaa
1                  5                        10
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:6:

```
Ser  Arg  Gly  Phe  Tyr  Val  Gln  Gln  Met  His  Ile  Ser  Leu  Glu  Ser
1                  5                        10                       15
```

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:7:

```
Ala  Arg  Ser  Phe  Phe  Ile  Gly  Gln  Ala  Asn  Val  Ala  Met  Val  Ser
1                  5                        10                       15
```

(2) INFORMATION FOR SEQ ID NO:8:

(i) SEQUENCE CHARACTERISTICS:
        (A) LENGTH: 15 amino acids
        (B) TYPE: amino acid (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:8:

```
Met  Val  Phe  Met  Glu  Gly  Asn  Gly  Arg  Ser  Phe  Tyr  Tyr  Lys  Leu
1              5                        10                       15
```

(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:9:

```
Gly  Xaa  Ser  Arg  Xaa  Phe  Xaa  Xaa  Xaa  Gln
1              5                        10
```

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

```
Trp  Tyr  Phe  Asp  Tyr  His  Trp  Asp  Arg  Thr  Pro  Ile  Ser  Arg  Ala
1              5                        10                       15
```

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

```
Arg  Pro  Trp  Asn  Asp  Lys  Ser  Pro  Lys  Asn  Leu  Trp  Tyr  Asn  Ser
1              5                        10                       15
```

(2) INFORMATION FOR SEQ ID NO:12:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:12:

```
Gly  Leu  Glu  Gly  Leu  Val  Pro  Glu  Gln  Met  Lys  Trp  Tyr  Asn  Ser
1              5                        10                       15
```

( 2 ) INFORMATION FOR SEQ ID NO:13:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:13:

```
Arg  Gly  Arg  Lys  Leu  Glu  Ser  Ser  Trp  Tyr  Asn  Thr  Val  Trp  Arg
1              5                        10                       15
```

( 2 ) INFORMATION FOR SEQ ID NO:14:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:14:

```
Thr  Glu  Ser  Pro  Gly  Trp  Asn  Val  Pro  Trp  Tyr  Gln  Val  Lys  Trp
1              5                        10                       15
```

( 2 ) INFORMATION FOR SEQ ID NO:15:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

```
Ile  Arg  His  Ala  Lys  Val  Pro  Trp  Tyr  His  Tyr  Pro  Gly  Gly  Arg
```

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:16:

```
Ala Gly Ser Tyr Trp Cys Lys Ala Trp Gly Leu Asp Cys Thr Ser
 1               5                  10                  15
```

(2) INFORMATION FOR SEQ ID NO:17:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:17:

```
Xaa Ser Xaa Trp Tyr Asn Thr Xaa
 1               5
```

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:18:

```
Ala Asp Gly Ala
 1
```

(2) INFORMATION FOR SEQ ID NO:19:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal ( x i ) SEQUENCE DESCRIPTION: SEQ ID NO:19:

Gly Ala Ala Gly Ala
1               5

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:20:

Xaa Cys Tyr Asn Lys Arg Lys Arg Ile His Ile Gly Pro Gly Arg Ala
1               5                   10                  15

Phe Tyr Thr Thr Cys
                20

( 2 ) INFORMATION FOR SEQ ID NO:21:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:21:

Xaa Cys Ser Ile His Ile Gly Pro Gly Arg Ala Phe Tyr Thr Thr Cys
1               5                   10                  15

( 2 ) INFORMATION FOR SEQ ID NO:22:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:22:

Ala Asp Gly Ala Xaa Xaa Xaa Xaa Xaa Xaa Xaa Xaa Xaa Xaa Xaa Xaa
1               5                   10                  15

Xaa Xaa Xaa Gly Ala Ala Gly Ala
                20

( 2 ) INFORMATION FOR SEQ ID NO:23:

( i ) SEQUENCE CHARACTERISTICS:
        ( A ) LENGTH: 24 amino acids (B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:23:

```
Ala  Asp  Gly  Ala  Xaa  Xaa  Xaa  Xaa  Xaa  Xaa  Xaa  Xaa  Xaa  Gly  Pro  Xaa
1                   5                             10                      15

Arg  Xaa  Xaa  Gly  Ala  Ala  Gly  Ala
               20
```

(2) INFORMATION FOR SEQ ID NO:24:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:24:

```
Ala  Asp  Gly  Ala  Leu  Leu  Xaa  Xaa  Xaa  Xaa  Xaa  Gly  Pro  Xaa  Arg  Xaa
1                   5                             10                      15

Xaa  Xaa  Xaa  Xaa  Leu  Leu  Gly  Ala  Ala  Gly  Ala
               20                        25
```

(2) INFORMATION FOR SEQ ID NO:25:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:25:

```
Ala  Asp  Gly  Ala  Cys  Xaa  Xaa  Xaa  Xaa  Xaa  Gly  Pro  Xaa  Arg  Xaa  Xaa
1                   5                             10                      15

Xaa  Xaa  Xaa  Cys  Gly  Ala  Ala  Gly  Ala
               20                   25
```

(2) INFORMATION FOR SEQ ID NO:26:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (iv) ANTI-SENSE: NO ( v ) FRAGMENT TYPE: N-terminal ( x i ) SEQUENCE DESCRIPTION: SEQ ID NO:26:

```
Ala Asp Gly Ala Cys Xaa Xaa Xaa Xaa Xaa Xaa Xaa Xaa Xaa Xaa
1               5                   10                      15
Xaa Xaa Xaa Xaa Cys Gly Ala Ala Gly Ala
            20              25
```

( 2 ) INFORMATION FOR SEQ ID NO:27:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

CUACUACUAC UAUCGAAAGC AAGCTGATAA ACCG         34

( 2 ) INFORMATION FOR SEQ ID NO:28:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

CAUCAUCAUC AUACAGACAG CCCTCATAGT TAGCG         35

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:29:

GTAAATGAAT TTCTGTATG AGG         23

( 2 ) INFORMATION FOR SEQ ID NO:30:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO

-continued ( i v ) ANTI-SENSE: NO ( x i ) SEQUENCE DESCRIPTION: SEQ ID NO:30:

CCCTCTAGAA ATAATTTTGT TTAACTTTAA GAAGGAGATA TACATATGGC CGACGGGGCT 60

( 2 ) INFORMATION FOR SEQ ID NO:31:

( i ) SEQUENCE CHARACTERISTICS:
( A ) LENGTH: 58 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

CTCAGATCTA TTAATGGTGA TGGTGATGAT GTATTTTGTC ACAATCAATA GAAAATTC 58

( 2 ) INFORMATION FOR SEQ ID NO:32:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:32:

Cys Asp Lys Ile
1

( 2 ) INFORMATION FOR SEQ ID NO:33:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:33:

Phe Ser Arg Asn Phe Phe Phe Ser Ala Gly Gln Gln Val Gln Met
1 5 10 15

HIV-SPECIFIC SYNTHETIC ANTIGENS AND THEIR USE

This is a continuation of application Ser. No. 08/323,338 filed on Oct. 14, 1994, now abandoned.

This invention relates to various antigenic compositions useful in treating AIDS and to methods of their use.

BACKGROUND OF THE INVENTION

Acquired Immune Deficiency Syndrome (AIDS) is the clinical manifestation of the infection of CD4 helper T-cells and other cell targets by human immunodeficiency virus (HIV). AIDS is characterized by opportunistic infections and certain malignancies. A similar disease, AIDS-related complex (ARC), shares many of the epidemiological features and immune abnormalities with AIDS, and often precedes the clinical manifestations of AIDS.

HIV has a unique collection of attributes: HIV targets the immune system; it possesses a reverse transcriptase capable of turning out highly mutated progeny; it is sequestered from the immune system; and it has hypervariable sequences in the (env) region. See, e.g., Hilleman, M. R. 1988, *Vaccine* 6:175 and Barnes, D. M., 1988, *Science* 240:719. One consequence of these attributes is the diversity of HIV serotypes.

The principal neutralizing determinant is an epitope residing in a hypervariable region of the (env) region. As a result, neutralizing antibodies directed against this epitope are generally extremely type-specific; that is, they neutralize only the parental virus and not other variants. Appropriate immunological therapies for AIDS require special consideration of this serological diversity.

Elicitation of neutralizing antibody is now regarded as one of the key consequential features in the successful design of an HIV immunological therapy. When a virus-specific antibody neutralizes its virus, it blocks the replication of the virus, but the precise mechanism is not fully characterized and is thought to vary with virus and target cell. See, e.g, Dimmock, N. J.,1987, *Trends in Biochem. Sci.* 12:70.

It would be most desirable to develop compounds which are vaccines and/or can be used to treat AIDS.

BRIEF DESCRIPTION OF THE INVENTION

This invention is directed to novel synthetic peptides which can be used as part of an anti-AIDS vaccine. These peptides mimic an epitope on the HIV protein gp120 which is a binding site of a neutralizing antibody. The peptides of this invention were selected out of a large random or semi-random array or library, based on their binding affinity to a known neutralizing monoclonal antibody, 19b. Monoclonal antibody 19b is also known as monoclonal antibody N7019b, and is described further in WO91/06575, published May 16, 1991 to Repligen Corporation and Louisiana State University; and C. F. Scott et al., 1990, *Proc. Natl. Acad. Sci USA* 87:8597–8601, both of which are incorporated by reference.

Thus, one aspect of this invention includes synthetic novel peptides useful as neutralization epitopes specific for HIV, known hereafter as Selected Principal Neutralization Epitopes (SPNEs).

Another aspect of this invention is the conjugation of SPNE peptides to a carrier to provide immunological conjugates useful as AIDS vaccines. The immunological conjugates of this invention are also useful for generating novel antibodies. In a preferred embodiment the antibodies so generated can neutralize HIV and be used as part of passive immunization therapies. The SPNEs of this invention and their immunological conjugates are also useful as reagents in viral assays, such as those used to screen donated blood.

The amino acid sequences of the preferred peptides of this invention are given in Table A, below. Each of these binds the broadly neutralizing human monoclonal antibody 19b, specific for the HIV principal neutralization determinant, and were selected and identified from oligopeptide epitope libraries. Each of these is useful as part of an immunological conjugate with the Outer Membrane Proteosome Complex of Neisseria (OMPC) to make vaccines against AIDS or ARC, and they may be also used in the production of other HIV-specific broadly neutralizing antibodies for passive immunity against AIDS or ARC. The SPNEs and their conjugates are also useful for the purpose of screening, clinical evaluation and diagnosis of AIDS and ARC as they may be part of assays used in the detection of HIV, or antibodies to HIV in blood samples.

TABLE A

I. Phage sequences Identified by Selection, with MAb 19b 19b.1009-6: Glu Val Asp Met Asp Gly Asn Arg Thr Phe Phe Tyr Val Gly Arg (SEQ.ID.NO.:1)
19b.1009-8: Ser Thr Glu Ile Leu Trp Met Gly Ser Gly Arg Gln Phe Tyr Met (SEQ.ID.NO.:2)
19b.1009-7: Ser Val Ile Met Leu Ala Pro Asp Arg Gly Phe Trp Arg Gly Glu (SEQ.ID.NO.:3)
19b.1009-10: Val Met Val Val Gly Met Asp Pro Gly Arg Ser Phe Phe Gly His (SEQ.ID.NO.:4)
Consensus: Xaa Yaa Yaa Xaa Met Xaa Pro Xaa Arg Xaa Phe Zaa Xaa (SEQ.ID.NO.:5) wherein Xaa is independently selected from any amino acid; Yaa is independently selected from Leu, Ile or Val; and Zaa is independently selected from Phe, Tyr, or Trp.

II. Phage Sequences Identified by Selection with MAb 19b in the Presence of Competing Peptide (SEQ. ID. NO.:20)

19bc-7-61: Ser Arg Gly Phe Tyr Val Gln Gln Met His Ile Ser Leu Glu Ser (SEQ.ID.NO.:6)
19bc-10-61: Ala Arg Ser Phe Phe Ile Gly Gln Ala Asn Val Ala Met Val Ser (SEQ.ID.NO.:7)
19bc-9-61: Met Val Phe Met Glu Gly Asn Gly Arg Ser Phe Tyr Tyr Lys Leu (SEQ.ID.NO.:8)
19bc-11-61: Phe Ser Arg Asn Phe Phe Phe Ser Ala Gly Gln Gln Val Gln Met (SEQ.ID.NO.:33)
Consensus: Gly Xaa Ser Arg Xaa Phe Zaa Yaa Xaa Gln (SEQ.ID.NO.:9) wherein Xaa is independently selected from any amino acid; Yaa is independently selected from any hydrophobic amino acid; and Zaa is independently selected from Phe, Tyr, or Trp.

III. Phage Sequences Identified by Selection with Mab 19b in the Presence of Competing Peptide (SEQ. I.D. NO.:21)

19b-13-712: Trp Tyr Phe Asp Tyr His Trp Asp Arg Thr Pro Ile Ser Arg Ala (SEQ.ID.NO.:10)
19b-14-715: Arg Pro Trp Asn Asp Lys Ser Pro Lys Asn Leu Trp Tyr Asn Ser (SEQ.ID.NO.:11)
19b-30-715: Gly Leu Glu Gly Leu Val Pro Glu Gln Met Lys Trp Tyr Asn Ser (SEQ.ID.NO.:12)
19b-40-715: Arg Gly Arg Lys Leu Glu Ser Ser Trp Tyr Asn Thr Val Trp Arg (SEQ.ID.NO.:13)
19b-26-715: Thr Glu Ser Pro Gly Trp Asn Val Pro Trp Tyr Gln Val Lys Trp (SEQ.ID.NO.:14)
19b-11-715: Ile Arg His Ala Lys Val Pro Trp Tyr His Tyr Pro Gly Gly Arg (SEQ.ID.NO.:15)
19b-49-715: Ala Gly Ser Tyr Trp Cys Lys Ala Trp Gly Leu Asp Cys Thr Ser (SEQ.ID.NO.: 16)
Consensus: Xaa Ser Yaa Trp Tyr Asn Thr Xaa (SEQ.ID.NO.:17) wherein Xaa is independently selected from any amino acid; and Yaa is any hydrophobic amino acid.

ABBREVIATIONS AND DEFINITIONS

| | |
|---|---|
| AIDS | Acquired immune deficiency syndrome |
| ARC | AIDS-related complex |
| conjugation | The process of covalently attaching two or more molecules each containing one or more |

TABLE A-continued

| | |
|---|---|
| | immunological determinants, e.g., HIV envelope fragments and OMPC |
| conjugate | Result of conjugation, also known as an antigenic conjugate or immunological conjugate. Co-conjugates are a special subgenus of conjugates. |
| Flanks | Flanking regions for SPNE. Such flanks are selected from either poly (Gly, Ser, Ala, Val) or a combination of amino terminal ADGA (SEQ.ID.NO.:18) and carboxy terminal GAAGA (SEQ.ID.NO.:19). |
| HIV | Generic term for the presumed etiological agent of AIDS and/or ARC, also referred to as strains HTLV-III, LAV, and ARV |
| Library | A collection of DNA or oligopeptide sequences, of defined length, with or without limited sequence restrictions |
| OMPC | Outer membrane proteosome complex |
| PCR | Polymerase chain reaction |
| poly (Gly, Ser, Ala, Val) | A linear, random polymer of amino acids selected from the group consisting of glycine, serine, alanine or valine. |
| SPNE | Selected Principal Neutralization Epitope, which is a principal neutralization determinant bound by one or more broadly neutralizing antibodies. SPNE may include consensus sequences. SPNE may have flanks. |

The terms "protein," "peptide," "oligopeptide," and "polypeptide" and their plurals have been used interchangeably to refer to chemical compounds having amino acid sequences of five or more amino acids.

When any variable occurs more than one time in any constituent or in Formula I (e.g. SPNE), its definition on each occurrence is independent of its definition at every other occurrence. Also, combinations of substituents and/or variables are permissible only if such combinations result in stable compounds.

SPNE peptides may exist alone as peptides, as internal sequences in proteins (e.g. phage pIII proteins), as part of an immunological conjugate with an outer membrane proteosome complex, or as a fragment of a recombinant fusion protein with an immuno-enhancer sequence such as Hepatitis B core. The position of the SPNE in a fusion protein may be N-terminal, internal or C-terminal.

DETAILED DESCRIPTION OF THE INVENTION

The present invention provides HIV Selected Principal Neutralization Epitopes of synthetic origin, immunological conjugates of these epitopes with a carrier such as OMPC, and methods of treating or preventing AIDS or ARC with these conjugates.

The epitopes of the present invention bind monoclonal antibody 19b, an HIV broadly-neutralizing antibody that binds gp120. The epitopes were identified by screening phage epitope libraries having randomly or semi-randomly generated epitope polypeptides accessible to monoclonal antibody 19b. The sequences of these polypeptides were deduced from their corresponding DNA sequences, determined by the polymerase chain reaction sequence analysis. The SPNE peptides, including consensus sequences thereof are characterized as having the sequences of Table A, (SEQ.ID.NO.:1–17 and 33) above.

The SPNE peptides of this invention also include any fragment of any of the sequences listed in Table A, above provided that the fragment is at least five amino acids in length.

The present invention also provides an effective immunogen against AIDS or ARC, and comprises an antigenic conjugate of the formula I

wherein:

SPNE is a Selected Principal Neutralization Epitope (SPNE) of HIV, said SPNE being a peptide comprising one or more amino acid sequences of Table A, (SEQ.ID.NO.:1–17 and 33) or fragments thereof, said fragment comprising at least five amino acids;

n is 1-200, wherein n is the number of polypeptides of SPNE covalently linked to OMPC;

~indicates covalent linkage; and

OMPC is the outer membrane proteosome complex of the microorganism Neisseria, said conjugate optionally substituted with an anion or polyanion to render it soluble such as polypropionic acid, or substituted with $A^-$, which is an anion or polyanion at physiological pH, said $A^-$ consisting of one to five residues of anions selected from the group consisting of carboxylic, sulfonic, propionic or phosphonic acid, or pharmaceutically acceptable salts.

This invention also includes a method of eliciting an antibody in an animal having an immune system capable of such a response, comprising administering to the animal the $(SPNE)_n$~(OMPC) conjugate of this invention; said conjugate optionally substituted with an anion or polyanion to render it soluble, or substituted with $A^-$, which is an anion or polyanion at physiological pH, said $A^-$ consisting of one to five residues of anions selected from the group consisting of carboxylic, sulfonic, propionic or phosphonic acid, or pharmaceutically acceptable salts. In this method, the animal is preferably a mammal, and more preferably a human. The phrase "having an immune system capable of such a response" it is intended to refer to the species of animal, and not intended to refer to whether a particular animal is immunocompromised. In a preferred method the antibody which is so elicited will neutralize the HIV virus.

Each conjugate molecule of formula I may have different peptides conjugated thereto, or, alternatively, multiples of a single peptide species conjugated thereto, or a combination.

The antigenic conjugates of this invention are prepared by isolating, synthesizing and purifying their component parts (SPNE and OMPC) then conjugating SPNE and OMPC together. Subsequent purification of conjugate mixtures may be performed as desired.

Large amounts of DNA coding for SPNE peptides may be obtained using polymerase chain reaction (PCR) amplification techniques as described in Mullins et al., U.S. Pat. No. 4,800,159 Innis, M. A. et al., 1990, *PCR Protocols* Academic Press, both of which are hereby incorporated by reference.

Once the DNA sequence is determined, its amino acid sequence can be deduced by translating the DNA sequence. The resulting amino acid sequence having the SPNE of the envelope gene is then employed to synthesize large quantities of SPNE peptides or a desired fragment thereof. Synthesis may be performed by organic synthesis or by recombinant expression systems, or both.

A. Preparation of Selected Principal Neutralization Epitope

1. Organic Synthesis of SPNE

Long peptides may be synthesized on solid-phase supports using an automated peptide synthesizer as described by Kent, S. et al., 1985 "Modern Methods for the Chemical Synthesis of Biologically Active Peptides", Alitalo, K. et al., (Eds.). *Synthetic Peptides in Biology and Medicine,* Elsevier pp. 29–57, which is hereby incorporated by reference. Manual solid-phase synthesis may be performed as described, for example, in Merrifield, R. B. J. 1963, *Am. Chem. Soc.* 85:2149, which is hereby incorporated by reference, or known improvements thereof. Solid-phase peptide synthesis may also be performed by the Fmoc method, which employs very dilute base to remove the Fmoc protecting group. Solution-phase synthesis is usually feasible only for selected smaller peptides. For preparing cocktails of closely related peptides, see, e.g., Houghton, R. A., 1985, *Proc. Natl. Acad. Sci. USA* 82:5131.

2. Expression of SPNE in a Recombinant Expression System

Cells transformed to express a SPNE gene may include bacteria such as *E. coli* or *B. subtilis,* yeasts, fungi, plant cells or animal cells. Expression vectors for many of these host cells are commercially available. The choice of host cell and expression vector are readily appreciated by those of ordinary skill in the art.

One preferred prokaryotic host cell is *E. coli*. Techniques for preparing recombinant *E. coli* cells is described in Wu, R (Ed), 1979 *Meth. Enzymol.* Vol. 68, and Maniatis, T. et al., 1982, *Molecular Cloning: A Laboratory Manual* Cold Spring Harbor.

Preferred eukaryotic systems include *Saccharomyces cerevisiae* as the host cells. *S. cerevisiae* and similar yeasts possess well known promoters useful in the construction of yeast expression systems, including but not limited to GAP491,GAL10, ADH2, and alpha mating factor. Yeast vectors include, but are not limited to, shuttle vectors, cosmids, chimeric plasmids, and those having sequences derived from 2-micron circle plasmids.

Recombinant mammalian expression systems are another preferred hosts for producing the recombinant SPNE for the conjugates of this invention. In general, a host mammalian cell can be any cell that has been efficiently cloned in cell culture, such as: Vero cells, NIH3T3, GH3, COS, murine C127 or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover, D. M. (ed.), 1985 *DNA Cloning: A Practical Approach,* Vols. I and II, IRL.

The SPNE gene of this invention comprises any DNA encoding 1) a SPNE of Table A, or 2) a fragment thereof comprising at least five amino acids in length. The SPNE gene may also include other features such as a promoter and/or operator, ribosome binding sites, termination codons, enhancers, terminators, or replicon elements. These additional features can be inserted into the vector at the appropriate site or sites by conventional splicing techniques.

The vector containing the appropriate gene coding for a SPNE, fragment or variant thereof is inserted into the host cell, by transformation or other means.

Recombinant SPNE may possess additional and desirable structural modifications not shared with the same organically synthesized peptide, such as adenylation, carboxylation, glycosylation, hydroxylation, methylation, phosphorylation or myristoylation. These added features may be chosen or preferred as the case may be, by the appropriate choice of recombinant expression system. On the other hand, recombinant SPNE may have its sequence extended by the principles and practice of organic synthesis of section A above.

B. Conjugation of SPNE and OMPC to Form a Covalent Linkage(s) Yielding Conjugate or Co-conjugate Antigenic conjugates of SPNE and OMPC are useful for vaccination, either pre- or post-exposure, to prevent or treat AIDS or ARC. Such conjugates have at least one covalent linkage between the antigenic SPNE and OMPC, and typically have more than one SPNE molecule covalently bound to each OMPC molecule.

SPNE and OMPC are prepared separately, then linked by non-specific cross-linking agents, monogeneric spacers or bigeneric spacers. Methods for non-specific cross-linking are well known and include, reaction with glutaraldehyde; reaction with N-ethyl-N'-(3-dimethylaminopropyl) carbodiimide, with or without admixture of a succinylated carrier; periodate oxidation of glycosylated substituents followed by coupling to free amino groups of a protein carrier in the presence of sodium borohydride or sodium cyanoborohydride; diazotization of aromatic amino groups followed by coupling on tyrosine side chain residues of the protein; reaction with isocyanates; or reaction of mixed anhydrides. See, generally, Briand, J. P. et al., 1985, *J. Imm. Meth.* 78:59.

In another embodiment of the invention, conjugates are formed with a monogeneric spacer. These spacers are bifunctional and require functionalization of only one of the partners of the reaction pair to be conjugated before conjugation takes place. By way of illustration rather than limitation, an example of a monogeneric spacer involves coupling the SPNE peptide to one end of the bifunctional molecule adipic acid dihydrazide in the presence of carbodiimide. A diacylated hydrazine presumably forms with pendant glutamic or aspartic carboxyl groups of SPNE. Conjugation then is performed by a second coupling reaction with carrier protein in the presence of carbodiimide. For similar procedures, see for example, Schneerson, R. et al., 1980, *J. Exp. Med.* 152:361. Another example of a monogeneric spacer is described in Fujii, N. et al., 1985, *Int. J. Peptide Protein Res.* 26:121.

In another embodiment of the invention, conjugates of SPNE and OMPC are formed with a bigeneric spacer. Bigeneric spacers are formed after each partner of the reaction pair to be conjugated, e.g., SPNE and OMPC, is functionalized with a bifunctional spacer. Conjugation occurs when each functionalized partner is reacted with its opposite partner to form a stable covalent bond or bonds. See, for example, Marburg, S. et al., 1986 *J. Am. Chem. Soc.*108:5282–5287; and Marburg, S. et al., U.S. Pat. No. 4,695,624, issued 22 Sep. 1987. Bigeneric spacers are preferred for preparing conjugates in human vaccines since the conjugation reaction is well characterized and easily controlled.

In another embodiment of this invention, co-conjugates are formed of SPNE and OMPC, wherein the OMPC is also covalently modified with a low molecular weight moiety (hereinafter referred to as "A$^{-}$") having an anionic or polyanionic character at physiological pH. "A-" is typically one to five residues of an anionic form of carboxylic, sulfonic, propionic or phosphonic acid. These co-conjugates are suitable for raising an anti-SPNE response, since the anions enhance solubility of conjugates in aqueous solutions. Their synthesis, detailed description and other advantages are described in EPO 467 700 of Leanza, W. J. et al.

Antigenic conjugates of OMPC and substituted peptide(s) of Table A are also within the scope of the present invention. The substituted peptides may be prepared using known procedures. Hetero-geneous products of the conjugation reaction are easily separable if needed by a variety of suitable column chromatography techniques.

C. Recombinant Fusion Polypeptides (RFPs)

To evaluate SPNE as immunogens, recombinant shuttle vectors coding for RFPs of novel SPNE and or fragments thereof, such as pIII (with or without a polyhistidine tail), Hepatitis B core, Hepatitis B surface antigen or protein A are made using known methods. Briefly, DNA sequences coding for a selected SPNE are ligated in-frame to DNA sequences coding for pIII, Hepatitis B core and/or surface antigen fusions, or protein A. The resulting DNA fragment may be expressed in any of a wide variety of readily available recombinant expression systems, e.g., $E.$ $coli$ BL21 (DE3).

In the alternative, the fusion peptides can be made by synthetic organic means, although this method is generally limited by feasibility and by practicality to smaller fusion peptides.

D. Vaccine Formulation

The form of the antigen within the vaccine may take various molecular configurations. A single molecular species of the antigenic conjugate $(SPNE)_n$–OMPC will often suffice as a useful and suitable antigen for the prevention or treatment of AIDS or ARC. Other antigens in the form of cocktails are also advantageous, and consist of a mixture of conjugates that differ by the degree of substitution (n) or the amino acid sequences of the SPNE peptides, or both. An immunological vector or adjuvant may be added as a vehicle according to conventional immunological testing or practice.

The conjugates of this invention, when used as a vaccine, are administered in immunologically effective amounts. Dosages of between 1 µg and 500 µg of conjugate, and preferably between 50 µg and 300 µg of conjugate are administered to a mammal to induce anti-peptide, anti-HIV, or HIV-neutralizing immune responses. About two weeks after the initial administration, a booster dose may be administered, and then again whenever serum antibody titers diminish. The conjugate should be given intramuscularly at a concentration of between 10 µg/ml and 1 mg/ml, and preferably between 50 and 500 µg/ml, in a volume sufficient to make up the total required for immunological efficacy.

Adjuvants may or may not be added during the preparation of the vaccines of this invention. Alum is the typical and preferred adjuvant in human vaccines, especially in the form of a thixotropic, viscous, and homogeneous aluminum hydroxide gel. One embodiment of this invention is the prophylactic vaccination of patients with a suspension of alum adjuvant as vehicle and a cocktail of $(SPNE)_n$–OMPC as the antigens.

E. Other Utilities

The SPNEs and their immunological conjugates of this invention are also useful in screening blood products for the presence of HIV antigen or HIV-specific antibody. Thus, $(SPNE)_n$–OMPC or SPNE can be readily employed in a variety of immunological assays, including radioimmunoassay, competitive radioimmunoassay, enzyme-linked immunoassay, and the like. For an extensive discussion of these types of utilities, see, e.g., U.S. Pat. No. 5,075,211.

F. Method for Screening Phage Epitope Libraries

Phage epitope libraries are unusually versatile vehicles for identifying new antigens or ligands. Typically, a small, randomly generated DNA sequence, e.g., 45 base pairs, which will generate exposed oligopeptide surfaces in the mature phage is inserted into a phage genome. Mature phages are mixed with a screening antibody of desired specificity; in the presence of the competing ligand, which may be an oligopeptide or polypeptide. Bound phages are then separated from unbound phage, and the bound phage is cloned and sequenced. A conventional example of a phage epitope library is the filamentous phage fd and its gene III coding for minor coat protein pIII. See, e.g., Parmley, S. F. et al., 1988, $Gene$ 73:305; and Scott, J. K. et al., 1990, $Science$ 249:386, which set forth extensive discussion and detail on construction of these libraries.

In one embodiment of the present invention, the competing oligopeptide ligand is either:
Nle-CsYNKRKRIHIGPGRAFYTTCs (SEQ.ID.NO.:20) or
Nle-CsSIHIGPGRAFYTTCs (SEQ.ID.NO.:21)
wherein "Cs" indicates a disulfide cysteine residue.

G. Combination Therapy

The vaccines of this invention may be effectively administered, whether at periods of pre-exposure and/or post-exposure, in combination with effective amounts of the AIDS antivirals, immunomodulators, anti-infectives, or vaccines. Examples of AIDS antivirals are: AL-721 from Ethigen (Los Angeles, Calif.); Recombinant human Interferon-Beta from Triton Biosciences (Alameda, Calif.); Acemann from Carrington Labs (Irving, Tex.); Ganciclovir from Syntex (Palo Alto, Calif.); d4T or ddI, both from Bristol-Myers (New York, N.Y.); EL10 from Elan Corp. (Gainville, Ga.); Foscarnet from Astra Pharmaceutical Products (Westborough, Mass.); 3-([4,7-dichloro-1,3-benzoxazol-2-yl)methyl]amino)-5-ethyl-6-methylpyridin-2(1H)-one or (N-(2(R)-hydroxy-1(S)-indanyl)-2(R)-phenylmethyl-4-(S)-hydroxy-5-(1-(4-(3-pyridylmethyl)-2(S)-N'-(t-butylcarboxamido)-piperazinyl))-pentaneamide, both from Merck & Co. (Rahway, N.J.); ddC from Hoffaman-LaRoche (Nutley, N.J.); Novapren from Novaferon Labs, Inc. (Akron, Ohio); Peptide T Octapeptide from Peninsula Labs (Belmont, Calif.); AZT or Alpha Interferon, both from Burroughs Wellcome (Research Triangle Park, N.C.); Rifabutin from Adria Laboratories (Dublin, Ohio); Destran sulfate from Ueno Fine Chem. Ind., Ltd. (Osaka, Japan); or Virazole from Viratek/ICN (Costa Mesa, Calif.). Immunomodulators which can be combined with the vaccines of this invention include: Advanced Biotherapy Concepts' (Rockville, Md.) antibody which neutralizes pH labile alpha aberant Interferon in an immunoadsorption column; AS-202 from Wyeth-Ayerst Labs (Philadelphia, Pa.); Bropirimine from Upjohn (Kalamazoo, Mich.); CL 246,738 from American Cyanamid (Pearl River, N.Y.); Tumor Necrosis Factor, Gamma Interferon or rCD4, all from Genentech (S. San Francisco, Calif.); Granulocyte Macrophage Colony Stimulating Factor from Genetics Institute (Boston, Mass.), Sandoz (E. Hanover, N.J.), Hoechst-Roussel (Somerville, N.J.), Immunex (Seattle, Wash.), or Schering Plough (Madison, N.J.); HIV Core Particle Immunostimulant from Rorer (Ft. Washington, Pa.); IL-2 from Cetus (Emeryville, Calif.) and Hoffman-LaRoche (Nutley, N.J.); Intravenous Immune Globin from Cutter Biologicals (Berkeley, Calif.); IMREG-1 or IMREG-2, both from Imreg (New Orleans, La.); Imuthiol diethyl dithio carbamate from Merieux Institute (Miami, Fla.); Alpha-2 Interferon from Schering Plough (Madison, N.J.); Methionine-enkephalin from TNA Pharmaceutical (Chicago, Ill.); MTP-PE from Ciba-Geigy Corp. (Summit, N.J.); Granulocyte Colony Stimulating Factor from Amgen (Thousand Oaks, Calif.); Recombinant soluble human CD4 from Biogen (Cambridge, Mass.); Interferon a from Hoffinan-La Roche; Soluble T4 from Smith, Kline & French Laboratories (Philadelphia, Pa.); or Thymopentin from Immunobiology Research Institute (Annandale, N.J.).

Anti-infectives which can be used in combination with the vaccine of this invention include: Clindamycin with Primaquine from Upjohn (Kalamazoo, Mich.); Fluconazole from Pfizer (New York, N.Y.); Nystatin Pastille from Squibb Corp. (Princeton, N.J.); Ornidyl from Merrell Dow (Cincinnati, Ohio); Pentamidine from LyphoMed (Rosemont, Ill.); Prirtexim from Burroughs Wellcome; Pentammidine isethionate from Fisons Corp. (Bedford, Mass.); Spiramycin from Rhone-Poulenc Pharmaceuticals (Princeton, N.J.); Intraconazole-R51211 from Janssen Pharmaceuticals (Piscataway, N.J.); or Trimetrexate from Warner Lambert (Morris Plains, N.J.).

Other suitable compounds which can be used together with the vaccines of this invention include: Recombinant Human Erythro-poietin from Ortho Pharmaceuticals (Raritan, N.J.); and Megestrol Acetate from Bristol-Myers (New York, N.Y.).

It will be understood that the scope of combinations of the antigenic conjugates of this invention with AIDS antivirals, immuno-modulators, anti-infectives or vaccines is not limited to those mentioned above, but includes in principle any combination with any pharmaceutical composition useful for the treatment of AIDS.

The following non-limiting Examples are presented to illustrate the invention.

EXAMPLE 1

Library Construction

A. Random Library

A phage library containing random 15 amino acid epitopes was constructed by the methods of Scott, J. K. et al., 1990, Science 249:386, which is incorporated by reference. Synthetic 110 bp BglI fragments were prepared containing the degenerate coding sequence $(NNK)_{15}$, wherein N stands for an equal mixture of G, A, T and C, and K stands for an equal mixture of G and T. The library was constructed by ligating the synthetic 110 bp BglI fragments in phage fUSE5 and transfecting E. coli cells with the ligation product by electroporation.

The resulting phage oligopeptide epitope library (also known as Library ALPHA) had a complexity of approximately $40 \times 10^6$ different epitopes. Flanking nucleotide sequences were added to enhance folding of the amino acid sequence.

B. Semi-Random Libraries

The following libraries were constructed in the same manner as Example 1A:

TABLE OF LIBRARIES

| LIBRARY | Peptide Sequence | Complexity | SEQ.ID.NO. |
| --- | --- | --- | --- |
| ALPHA | ADGAXXXXXXXXXXXXXXXGAAGA | $50 \times 10^6$ | SEQ.ID.NO.:22 |
| BETA | ADGAXXXXXXXXXGPXRXXGAAGA | $92 \times 10^6$ | SEQ.ID.NO.:23 |
| GAMMA | ADGALLXXXXXGPXRXXXXXLLGAAGA | $66 \times 10^6$ | SEQ.ID.NO.:24 |
| DELTA | ADGACXXXXXGPXRXXXXXCGAAGA | $45 \times 10^6$ | SEQ.ID.NO.:25 |
| EPSILON | ADGACXXXXXXXXXXXXXXXCGAAGA | $200 \times 10^6$ | SEQ.ID.NO.:26 |

X is any amino acid

Library BETA consists of random polypeptide sequences around the V3 loop region; library GAMMA adds terminal leucines for enhanced loop formation; library DELTA instead adds a terminal cysteine on each end for enhanced loop formation; library EPSILON is a control of any sequence with a cysteine loop.

The 19b monoclonal antibody tested in this invention was screened against the mixture of libraries ALPHA and EPSILON.

EXAMPLE 2

Bead Coating Procedure

Polystyrene beads (d=0.25 inch) were coated with between 1 and 10 µg of antibody per ml in 50 mM $Na_2 CO_3$, pH 9.6, 0.02% sodium azide. Beads were incubated in the antibody solution at 4° C. overnight. The next day the coated beads were washed three times with phosphate buffered saline and once with water. After washing, the antibody-coated beads were air dried and stored frozen at –20° C. until needed. Before use, the antibody-coated beads were coated with 10 mg/ml BSA (to block free sites on the plastic) in TTBS (50 mM Tris pH 7.5, 150 mM NaCl, 0.5% (v/v) Tween 20) for 4 or more hours. Each batch of beads was checked for antibody activity by its ability to bind $^{125}I$ protein A, before being used in a phage selection screen.

EXAMPLE 3

Stringent Phage Selection with Antibody-Coated Beads

A. First Method-Low Stringency

The random epitope phage library ALPHA was incubated at 4° C. overnight with gentle rocking, with antibody-coated beads in TTBS, 1 mg/ml BSA. Typically, a total volume of 1 cc containing about $10^{11}$ total phage was used. The next day the bead, containing bound phage, was washed 10 to 12 times in TTBS, in a volume of 10 cc per wash, at room temperature, with a gentle rocking motion, for 10 minutes per wash.

The liquid was carefully drained off the beads between each wash. After the last wash the bound phage were eluted off the beads by incubating for 5 minutes at room temperature in a minimal volume (typically 200 µl) of 0.1N HCl, adjusted to pH 2.2 with glycine, 1 mg/ml BSA. The solution with the eluted phage was neutralized by adding 12 µl of 2M Tris, pH unadjusted, per 200 µl phage solution. The eluted phage were then used to infect E. coli K91K cells. Infected cells were plated onto LB agar plates containing 40 µg/ml tetracycline. Since the phage carry a tetracycline resistance marker, only infected cells grow on the plates. Typically, one bead selected between 5000 and 100,000 independent phages. Phage were harvested and precipitated twice with PEG. The precipitated phage were then titered. Phage can be put through additional rounds of screening as described above.

B. Second Method-High Stringency

The random epitope library or semi-random library was incubated at 4° C. overnight with gentle rocking, with antibody-coated beads in TTBS, 1 mg/ml BSA in the presence of competing oligonucleotide ligand: either peptide Nle-CsYNKRKRIHIGPGRAFYTTCs (SEQ.ID.NO.:20) or peptide Nle-CsSIHIGPGRAFYTTCs (SEQ.ID.NO.:21) at a concentration of 1 µg/ml. Typically, a total volume of 1 cc containing on the order of $10^{11}$ total phage was used, corresponding to the complexity of the library×1000. The next day the bead containing the bound phage was washed 10 times in TTBS, in a volume of 10 cc per wash, at 65° C., with gentle rocking, for 10 minutes per wash. Note that 65° C. in TTBS does not destroy phage. This was followed by one wash at room temperature in TTBS pH 4.0. The liquid was carefully drained off the bead between each wash. Next, the bound phage were eluted off the bead by incubating for 5 minutes at room temperature in 200 µl of 0.1N HCl, adjusted to pH 2.2 with glycine, 1 mg/ml BSA. The phage solution was neutralized by adding 12 µl of 2M Tris, pH unadjusted. The eluted phage were then used to infect *E. coli* K91K cells. Infected cells were grown in 1×Luria broth containing 40 µg/ml tetracycline (250 cc) and incubated with shaking for 48 hours at 37° C. Phage were harvested and precipitated twice with PEG (polyethylene glycol). The precipitated phage were then titered and approximately $10^{10}$ of the first round selected phage were again incubated with an antibody coated bead, washed as described above, regrown and harvested. Three cycles of selection and growth were performed. *E. coli* infected with phage were plated as clonal isolates.

EXAMPLE 4

Screening of Selected Phage with Antibody Lifts

After 1 or more rounds of selection according to Example 3, the infected *E. coli* colonies were screened for the ability to bind antibody (using the same antibody as used to select the phage). This was done by growing the plates until the colonies reached a diameter of one to four mm, placing nitrocellulose disks onto the plates, lifting the disks and placing them in a solution of 10% evaporated milk, TTBS for 4 or more hours. After lifting, the plates containing the infected colonies were regrown for several hours at 37° C. and placed at 4° C. until needed. The nitrocellulose disks were then washed 2–3× in TTBS and placed in TTBS and 1% milk and 0.5 to 1 µg/ml antibody solution. They were then incubated at 4° C. overnight with gentle rocking. After incubation, the disks were washed 4× in 100 cc TTBS for 20 minutes with gentle rocking, and then incubated in TTBS and 1% milk and $I^{125}$ protein A (0.5 to 1 µ curie/ml) for 1-½ to 3 hours. The disks were again washed 4× in 100 cc TTBS for 20 minutes. They were placed on X-ray film for 12 to 72 hours. The film was developed and colonies corresponding to dark spots were picked. If the plates were too dense to pick isolated colonies, the picked colony(ies) was replated at a lower density and the screen repeated to get clonal isolates.

EXAMPLE 5

Alternate Sequencing Method

Phage infected *E. coli* K91K cells were grown overnight at 37° C. in 1× Luria broth, 40 µg/ml tetracycline with shaking. The cells were pelleted and 0.005 ml of supernatant fluid was used as the template in PCR reactions. Templates and oligonucleotide primers (primer 1008-1: 5'CUA CUA CUA CUA TCG AAA GCA AGC TGA TAA ACC G 3' (SEQ.ID.NO:27)—located 106 nucleotides upstream of the random insert, and primer 1009-2: 5'CAU CAU CAU CAU ACA GAC AGC CCT CAT AGT TAG CG 3' (SEQ.ID.NO.:28)—located 87 nucleotides downstream from the random insert) were reacted in a volume of 0.050 ml containing 50 mM KCl, 10 mM TrisHCl pH 8.3, 1.5 mM $MgCl_2$, 0.01% (w/v) gelatin, 100 µM each dNTP and 2.5 units of Taq polymerase. Reactions were overlaid with mineral oil and amplified in a thermal cycler for an initial 8 min. at 94° C. then 35 cycles of 30 sec. at 94° C., 1 min. at 55° C., and 2 min. at 72° C. followed by a 5 min. incubation at 72° C.

PCR products were cloned by reacting with uracil DNA glycosylase while annealing to the pAMP vector plasmid of the Clone Amp system. Competent *E. coli* DH5α cells were transformed with the annealed vector. Colonies were grown in 2× Luria broth plus 100 µg/ml ampillicin. Plasmid DNA was purified with the Magic Miniprep DNA purification system. Inserts were verified by BamHI/EcoRI digestion followed by electrophoresis in 1.5% agarose gels. Positive clones were sequenced using the SP6 promoter primer in a modification of the USB Sequenase version 2.0 protocol using $^{35}$S-Sequetide and electrophoresed in 6% sequencing gels at 70 W for 2 hr. The gels were dried and exposed to X-ray film overnight and the sequence was determined.

EXAMPLE 6

PCR Sequencing

Phage infected *E. coli* K91K cells were grown overnight at 37° C. in 1× Luria broth, 40 µg/ml tetracycline on a roller drum. The cells were pelleted and 1 µl of supernatant was used as the template in PCR reactions. The template was amplified using a 100-fold excess of one primer over the other. Template and oligonucleotide primers (Primer 1008 and Primer 1009, sequences which are underlined in Example 5) were reacted in a volume of 100 µl containing 50 mM KCl, 10 mM Tris-HCl pH 8.3, 1.5 mM $MgCl_2$, 0.01% (w/v) gelatin, 200 µM each dNTP, and 2.5 units Taq polymerase. Reactions were overlaid with mineral oil and amplified in a thermal cycler for an initial 8 min. 94° C. incubation, then 30 cycles of 30 sec. at 94° C., 1 min. at 55° C. and 2 min. at 72° C. followed by a 5 min. incubation at 72° C. The mineral oil was removed, 2 ml of water added to the reactions, and the sample centrifuged in a microconcentrator for 30 minutes at 1000 ×g. The retentate volume was brought to 2 ml with water and centrifuged as above. The retentate was then collected by centrifugation for 2 min. at 500 ×g. Retentate concentrations were determined by electrophoresis on a 1% agarose gel containing 0.5 µg/ml ethidium bromide and visualization under UV light. The retentate was dried along with enough limiting primer from PCR reaction or with internal primer 1059-5'GTA AAT GAA TTT TCT GTA TGA GG 3' (SEQ.ID.NO.:29) located 27 nucleotides downstream from insert to give a 5:1 primer:template molar ratio. The DNA/primer mixture was resuspended in 8 µl water and 2 µl Tris-Buffer (200 mM Tris HCl, pH 7.5, 100 mM $MgCl_2$, 250 mM NaCl). The primer and template were annealed, and chain-termination sequencing reactions were set up. A 6% sequencing gel was run at 60 W for approximately 1 hour and 30 minutes. The gel was dried and exposed to X-ray film overnight, and the sequence determined.

EXAMPLE 7

SPNE-pIII-(His)₆Fusions

The HIV/pIII fusion was expressed in *E. coli* using the T7 polymerase system from Rosenberg, A. H. et al., 1987, *Gene* 56:125. The plasmid pET-3a (commercially available from Novagen, Madison, Wis.) was digested with Xba I and BamHI and the 5 kb vector fragment isolated. The isolated vector fragment was ligated with the Xba I, Bgl II-digested HIV/pIII fusion prepared by polymerase chain reaction (PCR) of the candidate HIV fused phage clones.

Two synthetic DNA oligomers were used to amplify a portion of the phage pIII gene (including the HIV sequences) and append sequences which permit efficient expression and purification of the pIII product. The first synthetic DNA oligomer, 5'°CCCTCTAGAAATAATTTGTTTAACTT-TAAGAAGGAGATATACATATGGCCGACGGGGCT3' (SEQ.ID.NO.:30), has homology with the fused phage pIII gene with sequences encoding the mature amino terminus of Ala-Asp-Gly-Ala (SEQ.ID.NO.:18). PCR amplification from this site incorporates sequences encoding the mature pIII protein, and rebuilds the pET-3a vector from the Xba I site to the initiating methionine.

The second synthetic DNA oligomer, sequence 5'CTCA-GATCTATTAATGGTGATGGTGATGATG-TATTTTGTCACAATCAATAGAAAATTC3' (SEQ.ID.NO.:31) encodes the reverse strand of the carboxyl-terminal portion of pIII ending with residues Cys-Asp-Lys-Ile (SEQ.ID.NO.:32). PCR with this oligo rebuilds the fuse phage pIII gene up to the transmembrane domain and appends six histidine residues to the carboxyl-terminal isoleucine. The presence of the histidine residues facilitates purification of the pIII fusion protein by metal chelation chromatography [Hochuli, E. et al., 1987, *J. Chromat.* 411:177] using nitrilotriacetic acid (NTA) resin (available from Qiagen, Chatsworth, Calif.).

Expression of the pIII fusion is obtained by transforming the expression plasmid into *E. coli* strain BL21 (DE3) [Rosenberg, A. H. et al., supra; U.S. Pat. No. 4,952,496; Steen, et al., 1986, *EMBO J* 5:1099.] This strain contains the T7 phage RNA polymerase gene under control of the lac operator/promoter. Addition of isopropylthio-galactoside (IPTG) at culture $OD_{600}$=0.6–0.8 induces T7 RNA polymerase expression which transcribes pIII mRNA to high levels. This RNA is translated yielding pIII fusion protein which is harvested 3–4 hours post-induction and chromatographed on NTA resin.

EXAMPLE 8

Synthesis of Selected Oligopeptide

The oligopeptide 19b.1009-8 (SEQ.ID.NO.:2) is selected for immunological characterization. It is synthesized by the solid-phase method.

EXAMPLE 9

Extraction and Purification of OMPC

A. First Method

All materials, reagents and equipment were sterilized by filtration, steam autoclave or ethylene oxide, as appropriate; aseptic technique was used throughout.

A 300 gm (wet weight) aliquot of 0.5% phenol inactivated cell paste of Meningococcal group B11 was suspended in 1200 ml of distilled water by stirring magnetically for 20 minutes at room temperature. The suspended cells were pelleted at 20,000 ×g for 45 minutes at 5° C.

For extraction, the washed cells were suspended in 1500 ml 0.1M Tris, 0.01M EDTA Buffer pH 8.5 with 0.5% sodium deoxycholate (TED Buffer) and homogenized with a 500 ml Sorvall Omnimixer at setting 3 for 60 seconds. The resulting suspension was transferred to ten Erlenmeyer flasks (500 ml) for extraction in a shaking water bath for 15 minutes at 56° C. The extract was centrifuged at 20,000 ×g for 90 minutes at 5° C. and the viscous supernatant fluid was decanted (volume=1500 ml). The decanted fluid was very turbid and was recentrifuged to clarify further at 20,000 ×g for 90 minutes at 5° C. The twice spun supernatant fluid was stored at 5° C. The extracted cell pellets were resuspended in 1500 ml TED Buffer. The suspension was extracted for 15 minutes at 56° C. and recentrifuged at 20,000 ×g for 90 minutes. The supernatant fluids which contained purified OMPC were decanted (volume=1500 ml) and stored at 5° C.

B. Second Method

All material, reagents, equipment and filters were sterilized by heat, filtration or ethylene oxide, except for the K-2 ultracentrifuge which was sanitized with a 0.5% formalin solution. Overnight storage of the protein was at 2°–8° C. between steps. A 0.2µ sterile filtration was conducted just before the final diafiltration to ensure product sterility.

Two 600-liter batches of *Neisseria meningitidis* were fermented and killed with 0.5% phenol, then concentrated to roughly 25 liters using two 10 ft² 0.2µ polypropylene cross-flow filtration membranes. The concentrated broth then was diafiltered with 125 L of cell wash buffer (0.11M NaCl, 17.6 mM sodium phosphate dibasic, 23.3 mM $NH_3Cl$, 1.34 mM KCl, adjusted to pH 7 with 85% phosphoric acid followed by 2.03 mM magnesium sulfate heptahydrate).

For extraction, an equal volume of 2X-TED buffer (0.2M Tris, 0.02M EDTA adjusted to pH 8.5 with concentrated HCl, followed by the addition of 1.0% sodium deoxycholate) was added to the cell slurry. The resulting slurry was heated to complete the extraction of OMPC from the cells.

For further purification, the extracted cell slurry was centrifuged at 30,000 ×g (18,000 rpm) in a "one-pass" flow mode in a K-ultracentrifuge, and the supernatant stream was collected. The low-speed supernatant was concentrated to 10 liters on two 0.1-micron polysulfone autoclavable hollow-fiber membranes and collected in an 18 liter sterile bottle. The filtration equipment was given two 4-liter rinses with TED buffer (0.1M Tris, 0.01M EDTA, adjusted to pH 8.5 with concentrated HCl, followed by the addition of sodium deoxycholate to 0.5%) which was combined with the retentate. The retentate was subdivided into two or three equal parts. Each part was centrifuged at 80,000 ×g (35,000 rpm) for 30 minutes. The OMPC protein was pelleted, and the majority of soluble proteins, nucleic acids and endotoxins remained in the supernatant, which was discarded. The pelleted protein was resuspended by recirculating 55% 5° C. TED buffer through the rotor. The first high-speed resuspensions were combined and subjected to a second low-speed spin. The second low-speed spin ensured that residual cell debris was removed from the product stream. The second low speed supernatant was subdivided into two or three equal parts. Each fraction was given two consecutive high-speed spins. All high-speed spins were operated under the same conditions and each further purified the OMPC protein.

For sterile filtration and final diafiltration, the third high-speed resuspensions were diluted with an equal volume of TED buffer and filtered through a 0.2 micron cellulose acetate filter. When all fractions were permeated, an 8 L TED buffer rinse was used to flush the filtration system. The permeate and rinse were combined and concentrated to 3 liters on a 0.1 micron polysulfone autoclavable hollow fiber membrane. The material then was diafiltered with 15 liters of sterile pyrogen free water. The retentate was collected in a 4-liter bottle along with a 1 L rinse to give the final product. The final aqueous suspension was stored at 2°–8° C., as purified OMPC.

C. Third Method

OMPC is purified from 0.2M LiCl-0.1M Na acetate, pH 5.8 extracts by ultracentrifugation, by the method of C. E. Frasch et al., 1974 *J. Exp. Med.* 140:87–104.

EXAMPLE 10

Oligopeptide 19b.1009-8 (SEQ.ID.NO.:2) is conjugated to OMPC by the co-conjugation method of EPO 467 700 of Leanza, W. J. et al., to give (SEQ.ID.NO.:2)-OMPC conjugate, as follows:

A. Thiolation of OMPC

OMPC (43.4 mg, 10 ml) is pelleted by ultracentrifugation (43 K rpm, 2 h, 4° C). The pellet is resuspended in a sterile filtered (0.22 µm) solution of: pH 11, 0.1M borate buffer (4 ml), N-acetyl homocysteine thiolactone (45 mg), DTT (15 mg), and EDTA (85 mg).

The resulting solution is degassed and purged with nitrogen (process repeated 3×) and is stored under $N_2$ overnight at room temperature. The thiolation mixture is transferred to a centrifuge tube and topped with pH 8.0, 0.1M phosphate buffer (approximately 4.5 ml). The protein is pelleted via ultracentrifugation, resuspended in pH 8.0, 0.1M phosphate buffer, and is repelleted by ultra-centrifugation. This pellet is resuspended in 1× TED buffer, with a total resuspension volume of 7.0 ml. An Ellman's analysis on this solution (100 µl) reveals that it contains 0.961 mmol SH/ml solution (6.72 µmol SH total, 0.155 µmol SH/mg OMPC used).

B. Conjugation

The beta-maleimidopropionyl peptide (5.8 µmol) is dissolved in acetonitrile (1.0 ml) giving Solution P. A solution of beta-maleimidopropionic acid (5.5 µmol) in water (1.0 ml) is prepared, which is Solution M.

Thiolated OMPC (6.0 ml, 5.77 µmol), from in Step A, is transferred to a sterile 15 ml centrifuge tube. This solution is vortexed and solution M (420 µl, 2.31 µmol) added. The mixture is stirred briefly and allowed to age at room temperature (10 min.). Next, the reaction mixture is vortexed and solution P (596 µl, 3.46 µmol) added. The reaction mixture is vortexed briefly and allowed to age at room temperature for 2 h.

The conjugate is spun in a clinical centrifuge to remove any precipitated material. The supernatant is removed and the conjugate is pelleted by ultracentrifugation (43 K rpm, 2 h, 4° C.). The pellet is resuspended in TED buffer (total volume 6.5 ml), affording (SEQ.ID.NO.:2)-OMPC conjugate.

EXAMPLE 11

Immunization Protocol for SEQ.ID.NO.:2 -OMPC Conjugate

Four New Zealand white rabbits (2 to 2.5 kg) are immunized with the peptide (SEQ.ID.NO.:2)-OMPC conjugate vaccine (the vaccine) in the following manner: For time zero inoculations the vaccine is formulated into complete Freund's adjuvant (CFA) [1:1 (v/v) of CFA and 600 µg/ml of conjugate in saline]. Each dose (1.0 ml) consists of a total of 300 µg of vaccine. Each rabbit is inoculated with the vaccine preparation at two sites, by intramuscular (im) injection, in the upper hind leg. Two booster inoculations are given to each rabbit at week 4 and week 8 post initial injection. The vaccine for these booster injections is formulated into incomplete Freund's adjuvant. Each dose also consists of a total of 300 µg of vaccine.

Each rabbit is bled and sera is prepared by standard methods for anti-peptide ELISA tests (Example 13) and anti-HIV neutralization tests (Example 14). Sera collected represent time zero and biweekly intervals through week 14.

EXAMPLE 12

Measurement of Antibody Responses in Rabbits immunized with SEQ.ID.NO.:2-OMPC Conjugate Vaccine (ELISA)

Elicited anti-peptide antibody responses in vaccinated rabbits are determined by the use of an enzyme-linked immuno-adsorbent assay (ELISA). In this assay, microtiter plates are coated with about 0.5 µg peptide 19b.1009-8 (SEQ.ID.NO.:2) per well using an overnight incubation of peptide solution at 36° C. in a humidified atmosphere.

For ELISA tests, titers are determined with 0 time and weeks 2, 4, 6, 8, 10, 12 and 14 sera. Test sera are diluted 5-fold serially, are reacted for 1 hr with the peptide adsorbed wells, and are washed extensively. Positive results are identified after reactions of phosphatase-conjugated goat anti-rabbit sera with each well for 1 hr at 36° C., washing and the addition of a solution of 1.0 mg/ml p-nitro-phenyl phosphate (pNPP) in 10% diethanolamine, 0.5 mM $MgCl_2$ (pH 9.8) to each well. This last reaction proceeds for 30 minutes at room temperature and is stopped by addition of 3.0N NaOH. Absorbance at 405 nm is determined by using a plate reader.

EXAMPLE 13

Measurement of Virus Neutralizing Antibody Responses Elicited in Rabbits Immunized with SEQ.ID.NO.:2-OMPC Conjugates Neutralization of Infectivity in MT-4 Cells in vitro: For neutralization tests 2-fold serial dilutions of sera are made and 100 µL volumes are used in each test well in 96 well culture plates. All sera are heat-inactivated before use. Generally 1:10 is the starting dilution of sera. An aliquot of 100 µL virus stock dilution is added to each test well. The virus-antisera mixtures are incubated at 37° C. for 1 hr after which $1\times10^4$ MT-4 cells in 50 ml of culture medium are added to each well and the cultures are incubated for 7 days. The level of neutralization is determined by using the MTT dye reduction readout. MTT is added to each well to 500 µg/ml, incubated at 37° C. for 2 hr, and solubilized after addition of acid-isopropanol (0.04N HCl in isopropanol) to approximately 50% of the volume of each well. A clearly distinguishable bluish-purple color develops in wells containing viable cells that are protected from infection due to virus neutralization by anti-SEQ.ID.NO.:2 antibody whereas wells containing MT-4 cells killed by the infection remain yellow. The neutralization endpoints are determined as the last dilution of antisera preparation that prevents cell killing. Uninfected MT-4 cells are cultured with each test and a virus retitration are performed with each analysis.

What is claimed is:

1. An antigenic conjugate of HIV-specific, selected principal neutralization epitopes covalently linked to purified outer membrane proteosome of *Neisseria meningitidis*, wherein said conjugate is of the formula $$(SPNE)_n\text{~}(OMPC)$$

wherein:

SPNE is the Selected Principal Neutralization Epitope of HIV, which is a polypeptide of one or more amino acid sequences selected from the group consisting of amino acid sequences of SEQ.ID.NO.:1–17 and 33;

OMPC is purified outer membrane proteosome complex of *Neisseria meningitidis*, n is the number of polypeptides of SPNE covalently linked to OMPC and is 1–200;

~indicates covalent linkage.

2. The antigenic conjugate of claim 1 wherein the covalent linkage between SPNE and OMPC consists essentially of a bigeneric spacer.

3. An HIV-specific selected principal neutralization epitope polypeptide having any of the sequences selected from the group consisting of SEQ.ID.NO.:1–17 and 33.

4. An HIV-specific selected principal neutralization consensus polypeptide having any of the consensus sequences, said consensus sequences selected from the group consisting of amino acid sequences of SEQ.ID.NO.:5, 9, and 17.

5. The antigenic conjugate of claim 1 wherein said conjugate is substituted with $A^-$, which is an anion or polyanion at physiological pH, said $A^-$ consisting of one to five residues of anions selected from the group consisting of carboxylic, sulfonic, propionic, or phosphonic acid; or a pharmaceutically acceptable salt thereof.

* * * * *